United States Patent [19]

Heinz et al.

[11] 4,155,995
[45] May 22, 1979

[54] PETROLEUM BASED MOSQUITO LARVICIDE

[75] Inventors: Heinz D. Heinz, Pismo Beach; Steven J. Escobar, Oildale, both of Calif.

[73] Assignee: Witco Chemical Corporation, New York, N.Y.

[21] Appl. No.: 838,322

[22] Filed: Sep. 30, 1977

Related U.S. Application Data

[63] Continuation-in-part of Ser. No. 767,262, Feb. 10, 1977, abandoned, which is a continuation of Ser. No. 345,146, Mar. 23, 1973, abandoned.

[51] Int. Cl.$^2$ ............................................... A01N 9/00
[52] U.S. Cl. ................................................... 424/184
[58] Field of Search ........................ 424/168, 170, 184

[56] References Cited

U.S. PATENT DOCUMENTS

| | | | |
|---|---|---|---|
| 2,096,885 | 10/1937 | Donlan | 424/194 |
| 2,560,626 | 7/1951 | Bolssonou et al. | 424/170 |
| 2,774,709 | 12/1956 | Mayhew et al. | 424/170 |
| 2,988,473 | 6/1961 | Mallis et al. | 424/184 |
| 3,285,201 | 11/1966 | Maxwell | 424/168 |
| 3,499,969 | 3/1970 | Chamberg | 424/341 |

OTHER PUBLICATIONS

McCutcheon's "Detergents & Emulsifiers", 1970 Annual Allured Publ. Corp., Ridgewood, N.J., p. 83.
Ibid., p. 92.
Ibid., p. 221.
J. of Econ. Entomol., 60(2), 426–429, 1967, Micks et al.

*Primary Examiner*—Albert T. Meyers
*Assistant Examiner*—D. W. Robinson
*Attorney, Agent, or Firm*—Albert L. Gazzola; Morton Friedman

[57] ABSTRACT

A highly effective petroleum-based mosquito larvicide having dispersed therein minor amounts of a dialkyl polysiloxane and an ethoxylated mono-alkyl phenol.

6 Claims, No Drawings

PETROLEUM BASED MOSQUITO LARVICIDE

CROSS-REFERENCE TO RELATED APPLICATIONS

This application is a continuation-in-part application of application U.S. Ser. No. 767,262, filed Feb. 10, 1977, now abandoned which, in turn, is a continuation of U.S. application Ser. No. 345,146, filed Mar. 23, 1973 now abandoned.

BACKGROUND OF THE INVENTION

The killing of mosquito larvae and pupae by application of petroleum oil toxicants on their aquatic breeding grounds is well known. To be effective toxicants, particularly for insecticide-resistant strains, such as *Aedes nigromaculis* and *Culex tarsalis*, relatively high volumes of refined petroleum oils are generally applied on the aquatic breeding areas, e.g., 4–6 gallons per acre. At those volumes (concentrations), phytotoxicity and animal toxicity become problems, and often the resultant increase in larvae mortality is small or even negligible. Surfactants are sometimes added to the petroleum oils to increase their effectiveness as larvicides or pupicides.

U.S. Pat. No. 2,988,473 to Mallis et al., for insance, issued on June 13, 1961 and incorporated herein by reference, discloses a composition consisting essentially of a petroleum hydrocarbon oil having insecticidal properties and boiling in the range from 300° –800° F., and from about 0.001 to 2.0% by weight of a liquid organo-polysiloxane, e.g., dimethyl polysiloxane. According to the patent, the polysiloxane increases the insecticidal activity of the oil, and emulsions made with the oil, in household sprays for flies, cockroaches, mosquitos, moths, and the like. However, the use of a larvicidal petroleum oil boiling in the range of 500°–675° F., fortified with dimethyl polysiloxane, for instance, adds measurably nothing to the larvicidal or pupicidal activity of the petroleum oil at a volume application of about 2.0 gal/acre.

U.S. Pat. No. 3,499,969, issued to Chambers on Mar. 10, 1970, discloses a mosquito control oil consisting essentially of a hydrocarbon oil boiling between 400° and 800° F. and containing from about 0.2 to about 3.75 weight percent of a polyethoxylated 2,4-dinonyl phenol in which the component has an average of from about 6 to 14 ethoxy units. In columns 4 and 5 of this patent, scattered, it is indicated that the presence of aromatic hydrocarbons, such as the closely-related ethoxylated nonyl phenol or other surfactant, inhibit the larvicidal activity of the oil composition. Furthermore, and most importantly, the patent states that when ethoxylated nonyl phenol is present greater than normal amounts of the ethoxy dinonyl phenol are required to restore the original larvicidal activity. In other words, this patent teaches that ethoxylated nonyl phenol is not recommended as an additive to a petroleum larvicide or pupicide because it inhibits the toxicity of the oil composition. Moreover, in Table V, column 5, of this patent, it is shown that even ethoxylated dinonyl phenol, when it contains less than six ethoxy groups, exhibits seriously diminished larvicidal activities. This patent is also incorporated herein by reference.

Column 2, line 48-55, of Chambers is most dissuasive; "A number of other surfactants have been checked, and no other surfactant has been found to give the same effect as the ethoxylated nonyl phenols (9 species) and ethoxylated octyl phenols (5 species) with various numbers of ethoxy units in the substituent; ethoxylated amines (2 species); ethoxylated fatty acids (2 species); and 9 other ethoxylated materials."

Table II of the Chambers patent contrasts the activity of its claimed surfactant, i.e., ethoxylated (8) dinonyl phenol (EODP) (8), with the ethoxylated (5) octyl phenol claimed herein:

TABLE II

| Description of material | Interfacial tension dynes/cm. | Percent mortality, 24 hrs. exposure larvae | | |
|---|---|---|---|---|
| | | 1.25* | 2.5* | 5.0* |
| 500–600° F. paraffinic oil with 0.5 wt. percent ethoxylated (5) octyl phenol | 2.2 | — | 36 | 89 |
| 500–600° F. paraffinic oil with 0.375 wt. percent EODP (2) | 1 | 100 | 100 | — |

[1]Gallons per acre.
[2]EODP (8) is ethoxylated 2,4-dinonyl phenol having 8 ethoxy units (average).

According to the present invention, a high-boiling refined petroleum oil fortified with two specific surfactants each in a specific concentration range is made available; it has a low volume application, i.e., less than 2.5. gallons per acre, and preferably in the range of between 1 to 2 gallons per acre; it has excellent film-forming and spreading characteristics; it has low "mist volatility" when sprayed by aircraft; it produces a cohesive film of oil on the surface of a body of water; and it is an effective toxicant even against resistant strains of mosquito larvae, without destroying the surrounding animal and vegetable life. The oil alone, or the oil with one or the other surfactant, at this application rate is not as effective and thus unsatisfactory. The surfactants of the present petroleum oil composition are an ethoxylated mono-alkyl phenol having 2–5 ethoxy groups and a dialkyl polysiloxane, as hereinafter more fully described.

Generally, any refined petroleum oil of low aromatic content can be used in the present composition, such as a vacuum distilled, solvent extracted, fractionated and hydro-treated naphthenic raffinate having larvicidal activity, which, of itself, or when combined with either a dialkyl polysiloxane or an ethoxylated mono-alkyl phenol, is not an acceptable larvicide when applied on aquatic breeding grounds at the rate of less than about 2.5 gal/acre, but which, however, is very effective, particularly with regard to resistant strains of mosquito larvae, as stated above, when the larvicidal petroleum oil is combined with both the dialkyl polysiloxane and the ethoxylated mono-alkyl phenol within the concentration ranges hereinafter described and claimed. Combinations of other surfactants with petroleum oils are not as effective as larvicides, are often toxic to plants and animals, and are not part of the present larvicidal petroleum oil composition.

Larvicidal petroleum oils generally employed in the present composition are those derived from a neutralized naphthenic crude. They are generally refined by vacuum distillation, solvent extraction, fractionation and hydrogenation, and boil substantially within the range of about 500°–750° F., as described in U.S. Pat. No. 2,096,885, to Donlan, issued Oct. 26, 1937, for instance, or as described in U.S. Pat. No. 2,405,775, to Bradley, issued on Aug. 13, 1946. Refined mineral oils may be effectively employed herein, but are economically impractical for larvicidal use. It is particularly preferred to use a larvicidal vacuum distilled, solvent extracted, fractionated and hydro-treated naphthenic raffinate boiling in the range of about 550°–675° F., of low aromatic content, i.e., having an unsulfonated residue of over 90 and an API gravity of, for instance, between 25–31.

The composition of the present invention includes the larvicidal petroleum oil having dispersed therein a combination of about 0.3–2.0 weight percent of an ethoxylated $C_8$–$C_{12}$ phenol having 2–5, and preferably 3–4 ethoxy groups, and about 0.2–0.8 weight percent of a dialkyl polysiloxane, and preferably 1.0–1.2 and 0.3–0.4 weight percent of each, respectively.

It is an additional advantage of the present composition that it is stable under normal storage conditions, i.e., no evidence of separation of the surface active agents from the oil.

The preferred ethoxylated mono-alkyl phenol is nonyl phenol having 3–4 ethoxy groups, although generally $C_8$–$C_{12}$ mono-alkyl phenols having from 2–5 ethoxy groups, such as ethoxylated octyl, decyl and dodecyl phenol, for instance, can be employed in the present composition.

The dialkyl group of the polysiloxane may be lower alkyl, i.e., methyl, ethyl, propyl or isopropyl, for instance, but because dimethyl polysiloxane is readily available and less costly, it is particularly preferred. The higher alkyl substituted, i.e., over $C_5$, and aryl polysiloxanes, such as diphenyl polysiloxane, are not preferred because of cost, availability or both. Dialkyl polysiloxanes having a viscosity of about 50 cs at 25° C. are preferred for ease of dispersion in petroleum oil at ambient temperatures.

It is indeed surprising, in view of the teachings in U.S. Pat. No. 3,499,969, supra, that the presence of the preferred ethoxylated nonyl phenol, and one having 3–4 ethoxy groups, not only enhances the toxicity of the present composition as a larvicide when used in combination with a dialkyl polysiloxane, but in addition, it contributes to a well-balanced composition, which tests of aerial spraying show settles on the surface of a body of water as an effective cohesive larvicidal film.

The range of concentration of each surfactant in the petroleum oil, as set forth above, is effective and practical. That is to say that the present composition is not as effective a larvicide at the low volume application, supra, when quantities of surfactants fall below the lower, limits, and, although amounts above the upper limits are tolerated, it becomes impractical to use such excesses because the efficacy of the composition remains the same.

The mono-alkyl phenol/ethylene oxide condensation products are well known in the art and may be purchased under the trade names "Emcol (T24)", sold by Witco Chemical Corporation and "Surfonic N-40", sold by the Jefferson Chemical Company. The dialkyl polysiloxanes, particularly the preferred dimethyl polysiloxanes, are also well known and may be purchased under the trade name of "DC - 200 Fluid", manufactured by the Dow-Corning Company, preferably having a viscosity of about 50 cs at 25° C., as stated above.

Moreover, as also stated above, when only a di-alkyl polysiloxane additive is present, as disclosed in the Mallis et al. patent, supra, spreadability of the oil composition, when sprayed on a body of water at the rate of about 1–2 gallons per acre, is poor, and the larvae and pupae kill is not enhanced. Likewise when only the ethoxylated mono-alkyl phenol is present, cohesion of the oil composition on water is poor and the larvae and pupae kill is poor. The oil dispersion of the present combination of surfactants, in the specific concentration ranges, is, as stated above, well balanced, has an excellent spreading rate and excellent film coherence on a body of water, and quite unexpectedly the ethoxylated nonyl phenol additive, rather than inhibit toxicity of the petroleum oil, enhances the toxicity to larvae. Furthermore, the present preferred embodiment has no discernible phytotoxicity and/or animal toxicity, and can, therefore, be sprayed on water breeding areas without destroying surrounding vegetation and animal life, at the effective larvicidal dosage of less than 2.5 gallons per acre.

The present composition, as stated above, does not include the use of either surfactant alone, or any other surfactant or combination of surfactants. It includes only the combination of an oil-miscible ethoxylated long-chain mono-alkyl phenol having preferably 3–4 ethoxy groups and an oil-miscible dialkyl polysiloxane, in specific quantities as set forth hereinbefore, dispersed in a larvicidal petroleum oil, preferably of a low viscosity, i.e., under 200 SUS at 100° F. For aerial spraying, for instance, a petroleum oil having a viscosity of about 50–75 SUS at 100° F. is preferred.

Small quantities of other oil-miscible surfactants or toxicants, such as DDT, chlordane, lindane, malathion, and the like, or other additives which do not inhibit the larvicidal and pupicidal effects of the present composition, may be present without departing from the spirit of the present invention.

The following table summarizes the results of aerial spraying of a larvicide prepared according to the present invention and sprayed at the rate of (a) one gallon per acre and (b) two gallons per acre, respectively. The larvae population is determined both before and 24 hours after spraying, by sampling the same areas with a standard dipper. The larvae in the sample breeding areas are predominantly of the common species of mosquitos found in flooded pastures in California, such as *Culex tarsalis* and the *Aedes nigromaculis*, both species being resistant strains.

The larvicide is prepared by dispersing 1.0 weight percent and 0.3 weight percent, respectively, of ethoxylated nonyl phenol having 3–4 ethoxy groups (Emcol T-24) and dimethyl polysiloxane (DC - 200 Fluid) in a refined naphthenic raffinate, of low aromatic content, boiling in the range of 550°–675° F. and having a viscosity of 58 SUS at 100° F.

TABLE

| | 24 - Hour Larvae Kill at 1.0 Gal./acre LARVAE POPULATION | | | | | | |
|---|---|---|---|---|---|---|---|
| Location | No. of Dips | Total Larvae | Average Per Dip | No. of Dips | Total Larvae | Average Per Dip | % Mort. |
| A-Control* | 47 | 22 | 0.47 | 52 | 36 | 0.70 | — |
| B-Control* | 49 | 147 | 3.00 | 48 | 180 | 3.75 | — |
| C-Control* | 78 | 95 | 1.21 | 43 | 66 | 1.53 | — |
| | Before Treatment | | | After Treatment | | | |
| D | 81 | 105 | 1.30 | 153 | 9 | 0.06 | 96% |
| E | 81 | 93 | 1.15 | 144 | 17 | 0.12 | 90% |
| F | 26 | 58 | 2.23 | 109 | 4 | 0.04 | 98% |
| G | 75 | 113 | 1.54 | 105 | 4 | 0.04 | 97% |
| H | 26 | 27 | 1.04 | 87 | 2 | 0.02 | 98% |
| I | 24 | 19 | 0.79 | 9 | 0 | 0.00 | 100% |
| J | 13 | 4 | 0.03 | 20 | 0 | 0.00 | 100% |
| | At 2.0 Gal./acre | | | | | | |

TABLE-continued

| | 24 - Hour Larvae Kill at 1.0 Gal./acre LARVAE POPULATION | | | | | |
|---|---|---|---|---|---|---|
| Location | No. of Dips | Total Larvae | Average Per Dip | No. of Dips | Total Larvae | Average Per Dip | % Mort. |
| K | 52 | 160 | 3.00 | 70 | 0 | 0 | 100% |

*Control - No treatment (blind)

$$\% \text{ Mortality} = 100 - \left( \frac{\text{Average Larvae Per Dip After}}{\text{Average Larvae Per Dip Before}} \times 100 \right)$$

We claim:

1. A larvicidal composition comprising a larvicidal refined petroleum oil boiling in the range of about 500°–750° F. having dispersed therein from about 0.2–0.8 weight percent of a di-lower-alkyl polysiloxane and about 0.3 to 2.0 weight percent of an ethoxylated $C_8$–$C_{12}$ mono-alkyl phenol having 2–5 ethoxy groups.

2. A larvicidal composition as in claim 1, wherein the petroleum oil is a refined naphthenic raffinate boiling in the range of about 550°–675° F.

3. A larvicidal composition as in claim 1, wherein the ethoxylated $C_8$–$C_{12}$ mono-alkyl phenol is present at about 1.0–1.2 weight percent and the di-lower-alkyl polysiloxane is present at about 0.3–0.4 weight percent.

4. A larvicidal composition as in claim 1 wherein the dialkyl polysiloxane is dimethyl polysiloxane having a viscosity of about 50 cs at 25° C.

5. A larvicidal composition as in claim 1 wherein the $C_8$–$C_{12}$ mono-alkyl phenol is nonyl phenol.

6. A larvicidal composition as in claim 1 wherein 0.3 weight percent of dimethyl polysiloxane and 1.0 weight percent of ethoxylated nonyl phenol having 3–4 ethoxy groups are dispersed in said larvicidal petroleum oil.

* * * * *